United States Patent [19]

Mann

[11] Patent Number: 5,749,907
[45] Date of Patent: May 12, 1998

[54] SYSTEM AND METHOD FOR IDENTIFYING AND DISPLAYING MEDICAL DATA WHICH VIOLATE PROGRAMMABLE ALARM CONDITIONS

[75] Inventor: Brian M. Mann, Edgartown, Mass.

[73] Assignee: Pacesetter, Inc., Sylmar, Calif.

[21] Appl. No.: 801,281

[22] Filed: Feb. 18, 1997

[51] Int. Cl.$^6$ .................................................. A61N 1/37
[52] U.S. Cl. .................................................. 607/27; 128/903
[58] Field of Search ........................... 607/27; 128/903, 128/920, 923, 630, 697

[56]  References Cited

U.S. PATENT DOCUMENTS

3,960,140  6/1976  Buxton ................................. 128/903
5,464,012  11/1995  Falcone ............................... 128/630
5,513,645  5/1996  Jacobson et al. ...................... 607/27
5,669,391  9/1997  Williams .............................. 607/27

*Primary Examiner*—William E. Kamm

[57]  ABSTRACT

A system and method for identifying and displaying medical data items which violate programmable alarm conditions are provided. The system of the present invention automatically alerts the medical practitioner if changes or deviations in parametric and physiologic medical data items violate programmable alarm conditions. The system also provides the medical practitioner with the ability to edit, disable, and enable programmable alarm conditions associated with one or more parametric and physiologic medical data items. The system also allows the medical practitioner to select a range of medical data to be used when the determination of whether any alarm conditions were violated is made.

42 Claims, 8 Drawing Sheets

FIG. 1

| MEDICAL DATA ITEM | VISIT_1 mm/dd/yy | INTER-VISIT_1 | VISIT_2 mm/dd/yy | INTER-VISIT_2 | VISIT_3 mm/dd/yy | INTER-VISIT_3 | VISIT_4 mm/dd/yy |
|---|---|---|---|---|---|---|---|
| INTRINSIC ATRIAL RATE (IAR) | 95 BPM | 165, 190, 205 BPM | 110 BPM | 170, 184, 198 BPM | 85 BPM | 35, 38, 180 BPM | 89 BPM |
| ATRIAL LEAD IMPEDANCE | 190Ω | – | 320Ω | – | 440Ω | – | 1.8KΩ |
| MODE SWITCHES /DAY | – | 3 | – | 1 | – | 0 | – |
| BATTERY IMPEDANCE | 28KΩ | – | 29KΩ | – | 29.5KΩ | – | 32KΩ |

FIG-2

| BATTERY IMPEDANCE | X | BATTERY IMPEDANCE |
|---|---|---|
| BATTERY IMPEDANCE | | |
| BATTERY IMPEDANCE | | |

FIG-9

| MEDICAL DATA ITEM | ACTIVE 156 | LOWER_ALARM_THRESHOLD 160 | UPPER_ALARM_THRESHOLD 162 | BASELINE 164 | CHANGE_ALARM_THRESHOLD 170 |
|---|---|---|---|---|---|
| INTRINSIC ATRIAL RATE (IAR) | X | 40 BPM | 180 BPM | — | — |
| ATRIAL LEAD IMPEDANCE | X | 250 Ω | 1.5 KΩ | LINEAR REGRESSION OF HISTORICAL LEAD IMPEDANCE AT MEASUREMENT TIME MINUS 1 YEAR OR AT 2 MONTHS AFTER IMPLANT, WHICHEVER IS LATER | Δ(ATRIAL LEAD IMPEDANCE) > 250 Ω / IMPLANT TIME (IN YEARS) (ROUNDED UP) |
| MODE SWITCHES /DAY | | — | 2 SWITCHES | — | — |
| BATTERY IMPEDANCE | X | — | — | BATTERY IMPEDANCE FROM 1 YEAR EARLIER | Δ (BATTERY IMPEDANCE) > 2 KΩ |

SYSTEM AND METHOD FOR IDENTIFYING AND DISPLAYING MEDICAL DATA WHICH VIOLATE PROGRAMMABLE ALARM CONDITIONS

BACKGROUND OF THE INVENTION

This invention relates to implantable medical devices, and in particular to implantable medical devices that are capable of acquiring medical data—including physiologic data pertaining to a patient's medical condition, and parametric data relating to the device. More particularly, this invention relates to a system and method for identifying and displaying medical data which violate programmable alarm conditions.

Some implantable medical devices, such as pacemakers, defibrillators, and cardioverters (collectively referred to as implantable cardiac stimulating devices) are designed to monitor and stimulate the cardiac tissue of patients who suffer from cardiac arrhythmias. Using leads connected to the patient's heart, a cardiac stimulating device typically stimulates cardiac tissue by delivering electrical pulses in response to measured cardiac events which are indicative of a cardiac arrhythmia. Properly administered therapeutic electrical pulses often successfully reestablish or maintain the heart's regular rhythm. Implantable cardiac stimulating devices can treat a wide range of cardiac arrhythmias by using a series of adjustable parameters to alter the energy content, the shape, the location, and the frequency of the therapeutic pulses. The adjustable parameters are usually stored in a memory of the implantable device. The adjustable parameters can be defined or altered telemetrically by a medical practitioner using an implantable device programmer, such as the one disclosed in the copending, commonly assigned U.S. patent application Ser. No. 08/510,367, filed Aug. 2, 1995, of Snell and Levin, entitled "Improved User Interface for an Implantable Medical Device Using an Integrated Digitizer Display Screen," which is hereby incorporated by reference in its entirety.

After initial implantation and configuration of the implantable medical device, the medical practitioner typically performs periodic follow-up examinations to determine if the device is operating properly. On occasion, it may also be desirable for the medical practitioner to alter the device settings to improve the performance of the device. In order to make appropriate decisions regarding such changes, the medical practitioner should consider not only the current condition of the patient and the implantable medical device, but also historical information representative of changes to the patient's condition and changes in the operational characteristics of the implantable medical device.

Historical medical data should be taken into account because, while most implantable medical devices serve patients for years, certain physiologic and parametric changes having an impact on the performance of the device may occur during the time of service. These changes may include changes in characteristics of the patient's cardiac disorder, changes in the patient's course of drug therapy, changes in the patient's overall health, as well as changes in the operational characteristics of the implantable medical device (such as lead impedance and remaining battery life). In addition, medical knowledge about cardiac disorders and preferred methods of treatment may advance during the time of service.

Implantable device programmers have typically presented only the current physiologic and parametric data measurements, relying on separate computer systems (e.g., dedicated PC database computers, hospital mainframes, etc.) or paper files to serve as repositories for historical medical data. Thus, the patient's background information and historical medical data from previous visits had not been immediately available and had to be compiled into complex historical medical data reports, often through an error-prone manual process. One solution to the above problem involved integrating previously acquired medical data with the medical data acquired during the current visit, and organizing the integrated medical data in the form of a historical patient data file which is stored in a programmer, as disclosed in the copending, commonly assigned U.S. patent application Ser. No. 08/510,369, filed Aug. 2, 1995, of Snell, entitled "A System and Method for Storing and Displaying Historical Medical Data Measured by an Implantable Medical Device," which is hereby incorporated by reference in its entirety.

However, both historical medical data reports and the historical patient data file typically contain a large amount of information in numerical, textual, and graphical forms. As a result, when a historical medical data report or a historical patient data file is generated, the medical practitioner may not notice an important change or a deviation in one or more of the particular items of medical data because of the volume of information that must be considered. Thus, it would be desirable for the medical practitioner to be automatically alerted by the programmer during a follow-up visit to "unusual" changes or deviations in the medical data. Because courses of treatment for different patients may vary, it would also be desirable for the medical practitioner to have the ability to customize the automatic notification function for one or more medical data items from each patient's historical medical data, to correspond with each patient's course of treatment.

Most current implantable device programmers lack the ability to analyze historical medical data, instead forcing the medical practitioner to rely on secondary computer systems for medical data analysis. This approach to medical data analysis is problematic, because a medical practitioner would be better served if historical medical data could be analyzed during the follow-up visit. For example, a medical practitioner may wish to conduct a course of treatment for a particular patient which involves close monitoring of changes and deviations in specific medical data acquired during the current follow-up visit as compared to similar medical data acquired during previous follow-up visits. Currently, this objective must be accomplished by exporting the patient's medical data from the implantable device programmer to an external computer system for analysis—a procedure which is not practical during a follow-up visit. Thus, it would be desirable to provide the medical practitioner with the ability to perform comparative analyses of historical medical data during each follow-up visit. The medical practitioner can then make better-informed decisions about a patient's course of treatment at the time of the patient's visit.

SUMMARY OF THE INVENTION

In accordance with the present invention, a system and method are provided for identifying and displaying medical data items—including physiologic data items pertaining to a patient's medical condition, and parametric data items pertaining to the operational characteristics of an implantable medical device—which violate programmable alarm conditions. The system and method of the present invention utilize information processing and display capabilities of an implantable device programmer.

The present invention provides an implantable medical device equipped with data acquisition, data storage, and telemetric communication capabilities, and also provides an implantable device programmer, preferably in the form of a portable tablet computer, with data processing, data storage, graphical data display, data output, data communication, telemetric communication, and diagnostic capabilities.

At an initial follow-up visit, the system creates a historical patient data file for containing medical data. The medical data in the historical patient data file are updated during subsequent follow-up visits by integrating medical data acquired during each visit with the previously stored historical medical data. As a result, during a follow-up visit, the medical practitioner has access not only to recently acquired medical data (i.e., data acquired during the current visit and data acquired by the implantable medical device during the time between the current visit and the previous visit), but also to the historical medical data collected during earlier visits.

The historical patient data file contains medical data which may include physiologic data, parametric data, and other forms of medical data. Physiologic data and parametric data are stored in the form of data items, each data item representing a particular collection of values acquired over a period of time. Physiologic data items pertain to the patient's physical condition and may include, but are not limited to, information such as the patient's average heart rate over a period of time, the patient's activity and rate-response histograms, an image of the patient's surface electrocardiogram ("ECG"), and an image of the patient's intracardiac electrogram ("IEGM"). Parametric data items pertain to the implantable medical device operational characteristics and may include, but are not limited to, information such as remaining battery life and lead impedance of the sensing and pulse-delivering electrodes.

A master alarm table contains alarm conditions predefined by the manufacturer of the implantable device. When a new historical patient data file is created the master alarm table is duplicated and the copy is linked to the historical patient data file, where each parametric and physiologic data item may have one or more alarm conditions associated with it. Several schemes exist for long-term storage of the historical patient data file and the alarm table. For example, the historical patient data file and the alarm table may be stored in the implantable medical device, the implantable device programmer, or both. Each storage scheme has its own particular advantages and disadvantages. The above-incorporated U.S. patent application Ser. No. 08/510,369 provides several advantageous long-term historical patient data file storage schemes.

In a preferred embodiment of the present invention, the implantable device programmer acquires physiologic and parametric data from the implantable medical device through telemetry. The telemetric acquisition of data may also be performed remotely through a data communication pathway (e.g., a telephone line) if the patient with the implantable medical device has access to a remote telemetry device. The implantable device programmer may also take measurements and perform diagnostic tests by using its internal diagnostic circuitry and by using external equipment other than the implantable medical device. When new medical data are acquired during a follow-up visit, the new medical data may be analyzed, processed, and then integrated with the historical patient data file, which is then stored in accordance with one or more of the above-mentioned long-term storage schemes.

The implantable device programmer identifies and marks physiologic and parametric data items having values and changes which violate one or more of their associated alarm conditions. The medical practitioner may select a range of medical data to be analyzed by the implantable device programmer to determine whether any alarm conditions are violated. For example, the medical practitioner may select medical data from the last three visits for analysis. As a result, the system ensures that the medical practitioner is made aware of any unusual deviations and changes in the patient's condition or in the operational characteristics of the implantable medical device, even though these changes and deviations may not be apparent from an ordinary visual inspection of the medical data.

The historical patient data file may be graphically displayed—displaying medical data items having values and changes which violate the alarm conditions in an attention-attracting format in order to alert the medical practitioner. The historical patient data file may also be printed in a variety of formats.

The implantable device programmer also allows the medical practitioner to edit, disable, or enable the alarm conditions associated with each physiologic and parametric data item. Editing an alarm condition for a particular data item involves selecting a value or a formula for that alarm condition from a group of values and formulas provided by the manufacturer of the implantable medical device for that data item. Disabling a particular alarm condition causes the implantable device programmer to ignore that alarm condition, while enabling a disabled alarm condition causes the implantable device programmer to recognize that alarm condition.

Automatic notification of unusual deviations and changes in medical data items provides a solution for the difficulties associated with detecting such deviations in the large amount of medical data presented to a medical practitioner during a follow-up visit. The capability of editing alarm conditions allows the medical practitioner to tailor a specific set of alarm conditions for a particular patient. The capability of selecting a range of medical data from one or more previous follow-up visits, to be used in alarm condition analysis during the current follow-up visit, allows the medical practitioner to analyze a large amount of available historical medical data to aid in determining a course of treatment for a patient.

The present invention improves the medical practitioner's decision-making ability with regard to determining implantable medical device settings and selecting a course of therapy, by automatically alerting the medical practitioner during the follow-up visit to changes and deviations in medical data which violate the programmable alarm conditions.

BRIEF DESCRIPTION OF THE DRAWINGS

The above and other advantages of the invention will be apparent upon consideration of the following detailed description, taken in conjunction with the accompanying drawings, in which like reference numerals refer to like parts throughout, and in which.

DETAILED DESCRIPTION OF THE PREFERRED EMBODIMENT

Implantable cardiac stimulating devices are commonly used implantable medical devices and will be used to illustrate the principles of the present invention. It should be understood, however, that the principles of the present invention apply equally as well to other types of implantable medical devices, including devices which are intended to monitor a patient's physical condition.

Figure 1:
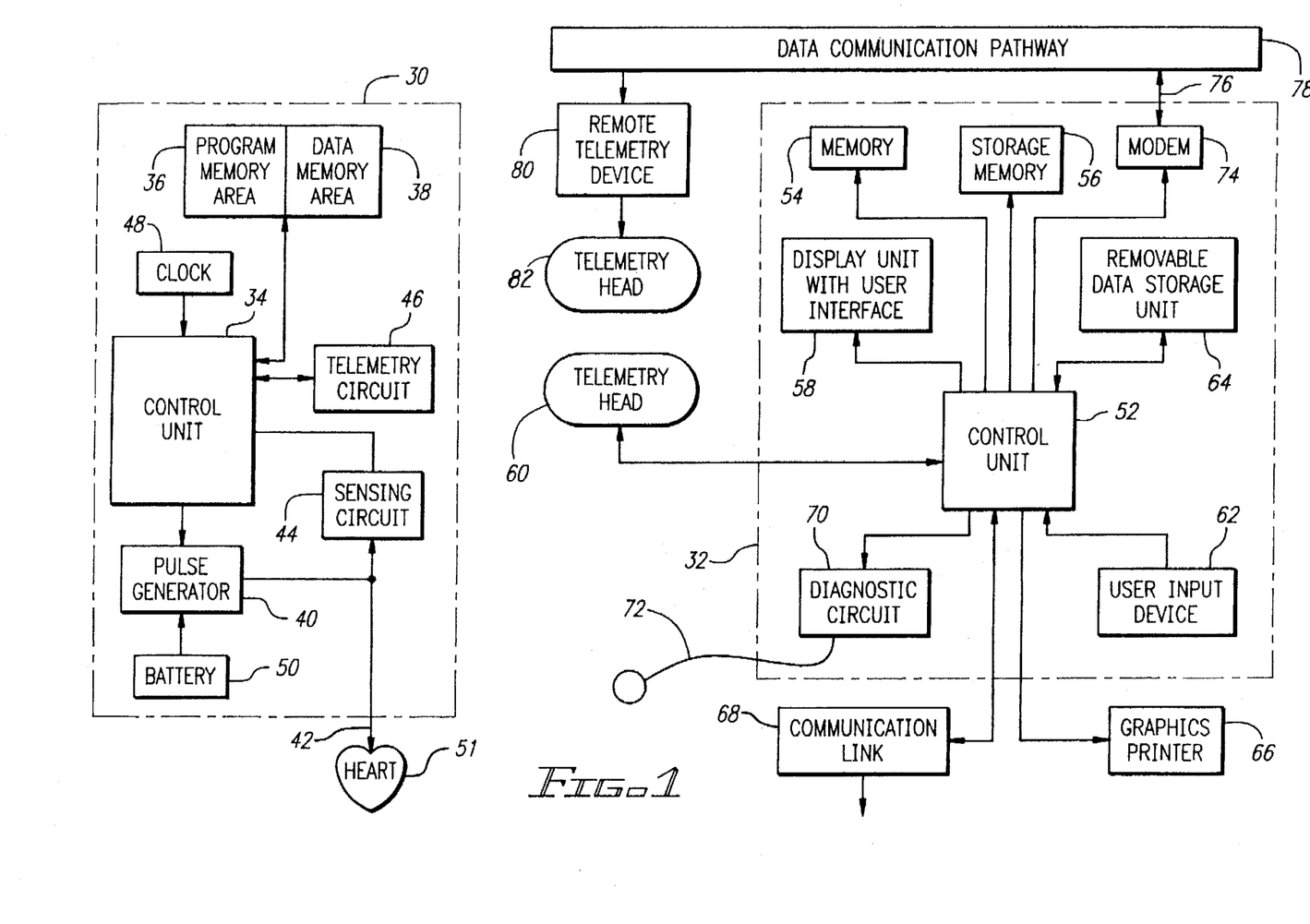
FIG. 1 is a schematic block diagram of a system for identifying and displaying historical medical data items which violate programmable alarm conditions in accordance with the principles of the present invention.

An implantable medical device 30 and an implantable device programmer 32 in accordance with this invention are shown in FIG. 1. The implantable medical device 30 may be a pacemaker, a cardioverter/defibrillator, or a combination of both. The operation of the implantable medical device 30 is controlled by a control unit 34, which preferably contains control circuitry (not shown) and a microprocessor (not shown) for executing control program instructions that are stored in a program memory area 36. A unique identifier code (UIC), which is preferably a manufacturer's serial number, is also stored in the program memory area 36. The UIC identifies the implantable medical device 30 as a device implanted in a particular patient. A data memory area 38 is provided for storing medical data (i.e., data collected by the implantable medical device 30 between visits). The program memory area 36 and the data memory area 38 may be memory blocks in a single memory unit (shown as a combination of program memory area 36 and the data memory area 38) or may be two separate memory circuits.

The control unit 34 also includes self-diagnostic circuitry (not shown) for monitoring the operational characteristics of the implantable medical device 30. Such operational characteristics include, but are not limited to, battery voltage, battery current, internal battery impedance, and lead impedance. The operational characteristics may be monitored by the implantable medical device 30 between visits. An example of how data pertaining to certain operational characteristics may be acquired between visits is disclosed in commonly assigned U.S. Pat. No. 5,507,786, issued Apr. 16, 1996, of Mann and Morgan, entitled "System and Method for Measuring and Storing Parametric Data Pertaining to Operating Characteristics of an Implantable Medical Device," which is hereby incorporated by reference in its entirety.

A pulse generator 40 is connected to a patient's heart 51 with at least one lead 42. The lead 42 is used for cardiac data acquisition (i.e., sensing the patient's intracardiac electrogram, or IEGM), as well as for delivery of therapeutic pulses. Therapeutic pulses may be pacing pulses delivered to maintain a normal heart rate, or higher energy shocks delivered to interrupt an occurrence of a tachycardia or fibrillation. The pulse generator 40 generates therapeutic pulses administered through the lead 42 to the patient's heart 51 under direction from the control unit 34. A sensing circuit 44 converts analog data acquired by the lead 42 into digital form which is capable of being analyzed by the control unit 34. The data is stored in the data memory area 38, and transmitted to the programmer 32 by telemetry through an internal telemetry circuit 46. A real time clock 48 is used to provide timing for monitoring cardiac events and for timing the application of therapeutic pulses by the pulse generator 40. A battery 50 supplies the necessary power to the pulse generator 40 (and to other components of the implantable medical device 30 through connections that are not shown).

In a preferred embodiment, the programmer 32 is a pen-based tablet computer such as the one disclosed in the above-incorporated U.S. patent application Ser. No. 08/510, 367. The pen-based tablet computer is advantageous for use in the context of the present invention because of its portability and its graphical user interface with extensive graphical display capabilities. Of course, other types of programmers, especially those capable of displaying graphics, may be used.

The programmer 32 is controlled by a control unit 52, which is preferably microprocessor-based. A programmer memory 54 (preferably random access memory) is used by the control unit 52 for software operation and data processing, while a storage memory 56 is used for long-term data storage. The storage memory 56 may be any type of memory suitable for long-term data storage including a hard disk drive, flash memory, or a rewritable optical disk. A table of unique identifier codes (UICs) is stored in the storage memory 56 with each particular UIC entry associated with a corresponding historical patient data file.

The programmer 32 is also provided with a graphical display unit 58. The display unit 58 is used to display recently acquired medical data obtained from the implantable medical device 30, as well as selected portions of the historical patient data file. An external telemetry head 60 is used to communicate with the implantable medical device 30 through conventional telemetry.

The medical practitioner interacts with the programmer 32 through a user input device 62, which may be a keyboard, a pen, or even a voice interface. A removable data storage unit 64, such as a floppy disk drive, is also provided for exporting data from the storage memory 56 or the programmer memory 54. One type of data that may be exported is the historical patient data file which the medical practitioner may want to give to a traveling patient, or save as a "back-up" copy, in case the original file becomes corrupted.

An external printer 66 is used to print graphical or textual data at the medical practitioner's request. An optional communication link 68 may be used to connect to separate computer system, such as a hospital mainframe (not shown) or a dedicated PC database computer (not shown) for transferring data to and from the programmer 32. The communication link 68 may be a physical connection, or a remote connection such as an infrared, a radio frequency, or a cellular link. A diagnostic circuit 70 converts analog data acquired by a plurality of external leads 72 into digital form. The digital data may be analyzed by the control unit 52 and stored in the programmer memory 54. A power source for the programmer 32 may be an on-board battery (not shown) or a power cord (not shown) connected to an electrical power outlet (not shown).

As an alternative to conventional telemetry, a modem 74 enables the programmer 32 to communicate telemetrically with the implantable device 30 through a data communication pathway 78 (which may be a typical public telephone line, an infrared link, or a cellular link) and a remote telemetry device 80. A data communication link 76 is used to connect the modem 74 to the data communication pathway 78. The data communication link 76 may be a physical connection or a cellular antenna. The remote telemetry device 80 is equipped with a telemetry head 82 for communicating with the implantable medical device 30 through telemetry.

The acquisition, processing, display, and storage of medical data are controlled by the programmer 32 through a control program (described below in connection with FIGS. 4–7).

Figure 2:
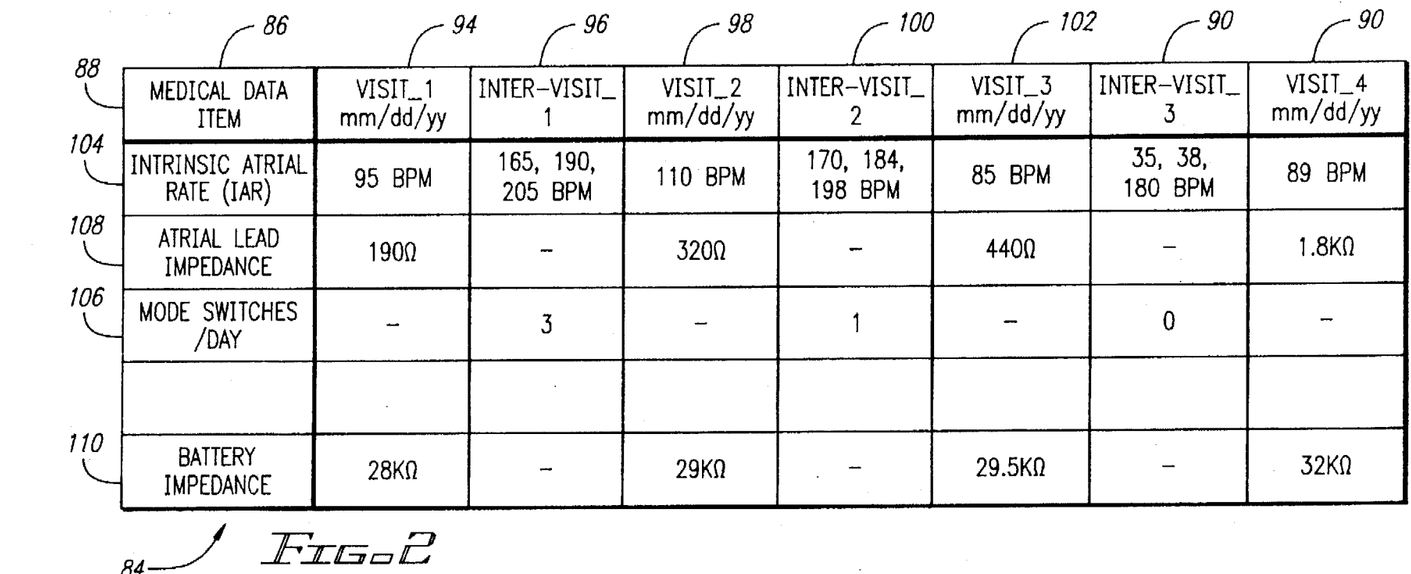
FIG. 2 depicts a portion of a historical patient data file containing recently acquired and historical medical data in accordance with the principles of the present invention.

Referring now to FIG. 2, a portion of a typical historical patient data file is shown. A unique historical patient data file is preferably stored in the storage memory 56 (FIG. 1) for each patient. This file stores medical data of several types such as physiologic data, parametric data, identification data, and comments. A table 84 is representative of the physiologic data and parametric data portions of the historical patient data file, which are preferably stored as a collection of individual data items, each data item representing a particular collection of values acquired over a period of time.

The table 84 includes a column 86 which identifies particular physiological and parametric data items. The data item table 84 also includes a row 88 which identifies one or more data acquisition time columns representative of particular follow-up visits and of inter-visit periods, for organizing data associated with each data item. Each data acquisition time column representative of a follow-up visit is associated with a real-time date.

Medical data may be classified as being recently or previously acquired. Recently acquired data are data stored in data acquisition time columns 90 and 92. The data acquisition time column 90 represents data acquired between the current visit and the previous visit, while the data acquisition time column 92 represents data acquired during the current visit. Previously acquired data are data stored in data acquisition time columns 93–102 and represent medical data acquired during, and between prior visits. For example, previously acquired data for the intrinsic atrial rate data item row 104 includes values of 95, 165, 190, 205, 110, 170, 184, 198, and 85 bpm (values stored in data acquisition columns 94–102 ), while recently acquired data for the intrinsic atrial rate data item includes values of 35, 38, 180, and 89 bpm (values stored in data acquisition columns 90–92 ). The amount of the data acquisition time columns in table 84 may vary from patient to patient, because new data acquisition time columns are added with each follow-up visit. For example, for a patient having four total follow-up visits, table 84 will contain seven data acquisition time columns (columns 90–102 ).

Physiologic data items identified in the column 86 pertain to the patient's physical condition and may include, but are not limited to, information such as the patient's average heart rate over a period of time, information representative of the patient's IEGM, and records of various pacing events that may have occurred between visits or during a visit. For example, "intrinsic atrial rate" and "mode switches per day," represented by rows 104 and 106 respectively, are physiologic data items. Physiologic data may be measured, for example, by the implantable medical device 30 (FIG. 1) through the lead 42 (FIG. 1). In addition to cardiac electrical activity, cardiac mechanical activity may be measured as described in copending, commonly assigned U.S. patent application Ser. No. 08/091,636, filed Jul. 14, 1993, of Causey and Moberg, entitled "Implantable Leads Incorporating Cardiac Wall Motion Sensors and Method of Fabrication and a System and Method for Detecting Cardiac Arrhythmias Using a Cardiac Wall Motion Sensor Signal." Physiologic data may also be measured by the programmer 32 (FIG. 1) through the plurality of external leads 72 (FIG. 1) (e.g., a surface ECG).

Physiologic data items are used by the medical practitioner to evaluate the patient's condition and the effectiveness of implantable medical device therapy. Physiologic data items detailing the patient's responses to particular settings of the implantable medical device 30 (FIG. 1) may be tracked over several visits. Such data items may facilitate the medical practitioner's selection of the settings for the implantable medical device 30 (FIG. 1) and may therefore affect the course of cardiac therapy. Undesirable side effects of implantable medical device therapy may also be ascertained by the medical practitioner when physiologic data items are examined.

Parametric data items identified in the column 86 pertain to the operational characteristics of the implantable medical device 30 (FIG. 1), such as the programmed settings of the implantable medical device 30 (FIG. 1), and the results of diagnostic tests that are either performed by the implantable medical device 30 (FIG. 1) automatically, or that are initiated by the medical practitioner through the programmer 32 (FIG. 1). Parametric data items may include, but are not limited to, information such as remaining battery life, AV delay, pulse width, pulse energy content (i.e., voltage and current), and lead impedance of the sensing and pulse-delivering leads (e.g., the lead 42 (FIG. 1)). For example, "atrial lead impedance" and "battery impedance," represented by rows 108 and 110 respectively, are parametric data items.

Parametric data items are important to the medical practitioner because such data items demonstrate the condition and overall performance of the implantable medical device 30 (FIG. 1) and its internal components over a period of time. For example, by examining parametric data items, the medical practitioner may be alerted to a potential problem if a parametric data item indicates that the impedance of the lead 42 (FIG. 1) connecting the implantable medical device 30 (FIG. 1) to the heart 51 (FIG. 1) significantly increased since the previous visit. Parametric data items also aid the medical practitioner in evaluating the effect of implantable medical device therapy and in determining future settings for the implantable medical device 30 (FIG. 1). The medical practitioner's decision-making ability may be further enhanced by evaluating the relationship between the patient's condition (as demonstrated by physiologic data items), and the settings of implantable medical device 30 (FIG. 1) (as demonstrated by parametric data items).

Before describing the operation of the control program (described below in connection with FIGS. 4–7), it would be helpful to define and identify alarm conditions for physiologic and parametric data items, and to describe how the alarm conditions are stored. Alarm conditions are criteria associated with particular physiologic and parametric data items which when met, notify the programmer control unit 52 (FIG. 1) of "unusual" values of, or "unusual" changes in, the associated physiologic and parametric data items. A particular alarm condition is violated when a value of, or a change in an associated physiologic or parametric data item is "unusual" as defined by the alarm condition.

The alarm conditions are preferably predefined constants or dynamic functions of one or more variables, such as time.

Examples of alarm conditions include, but are not limited to, a lower alarm threshold, an upper alarm threshold, and a change alarm threshold. One or more alarm conditions may be associated with each data item. For example, one data item may have only the lower alarm threshold, while another data item may have both lower and upper alarm thresholds, as well as the change alarm threshold.

Figure 3:
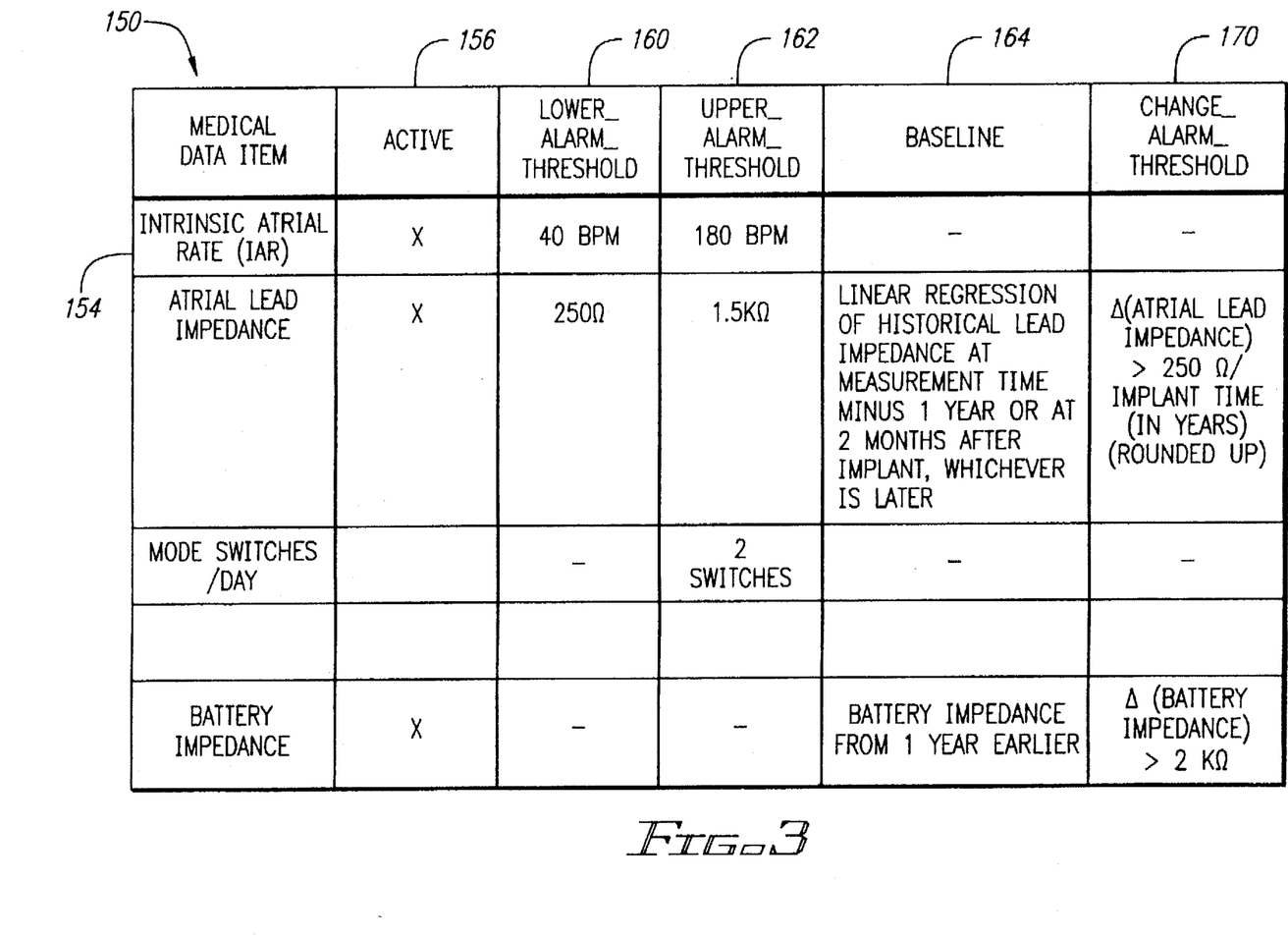
FIG. 3 depicts an alarm table which contains the alarm conditions in the form of programmable thresholds and baselines in accordance with the principles of the present invention.
Figure 4:
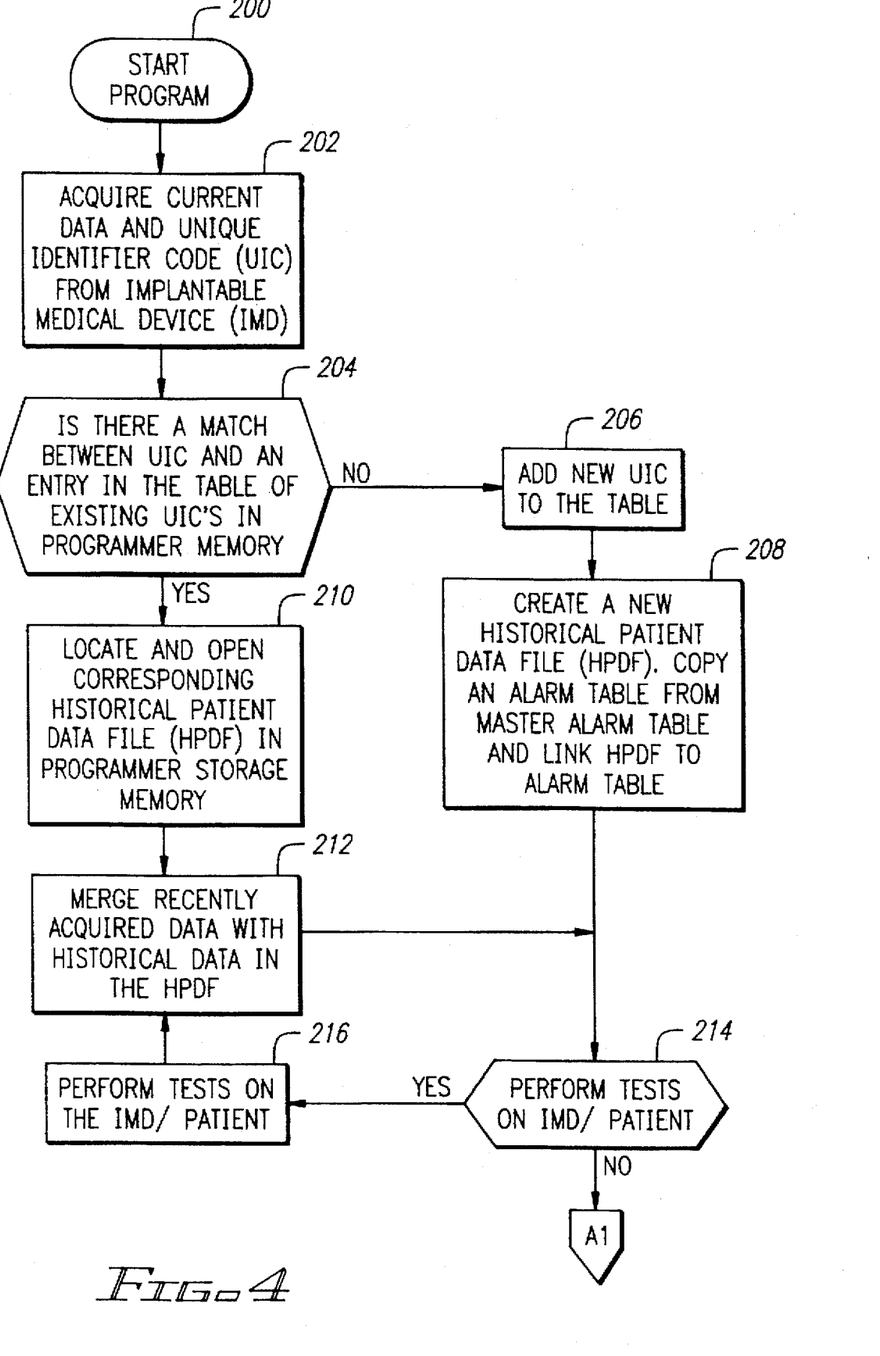
FIGS. 4–7 depict a logic flow diagram representative of a control program executed by the implantable device programmer which is used to identify and display medical data which violate programmable alarm conditions in accordance with the principles of the present invention.
Figure 5:
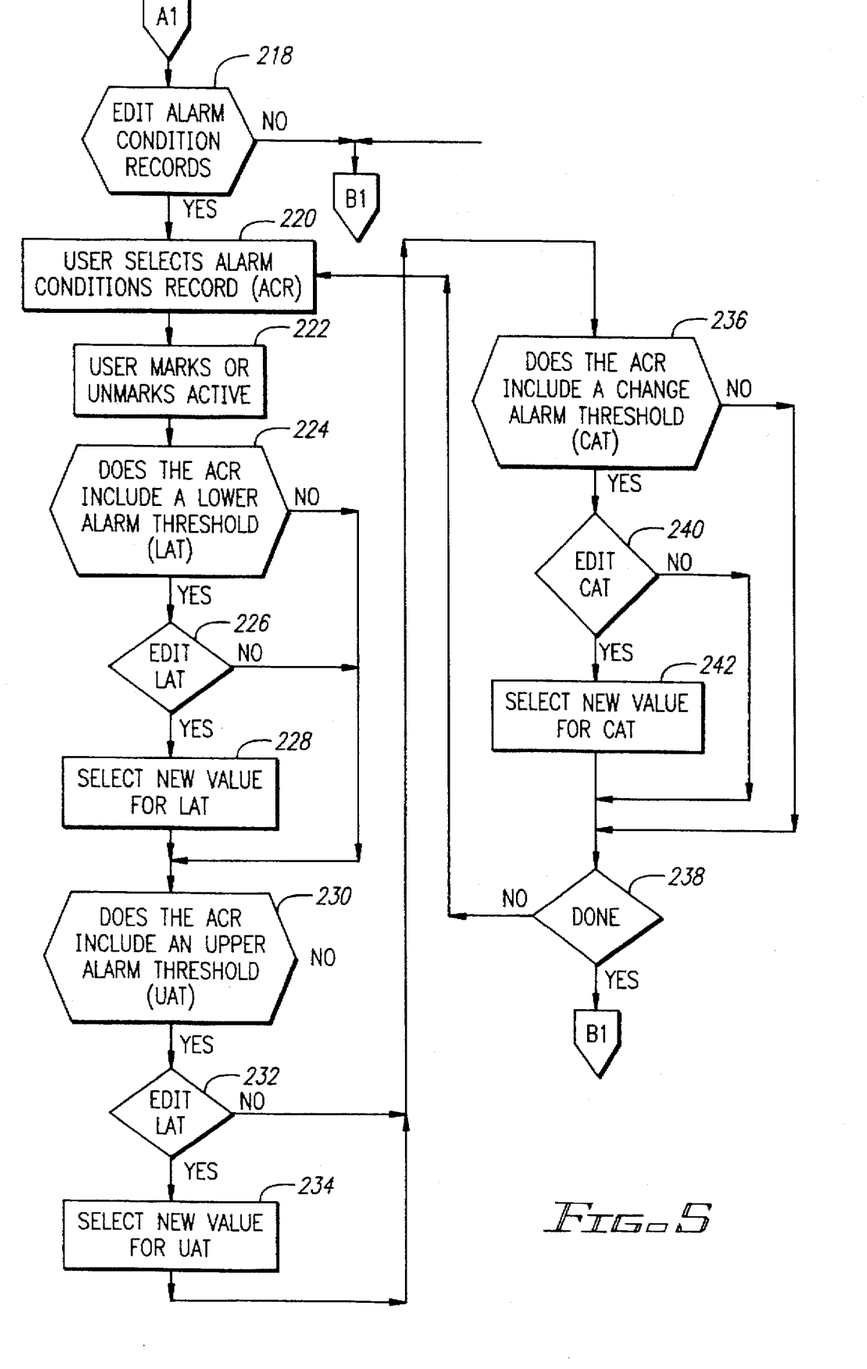

Referring now to FIG. 3, an alarm table 150 is used in accordance with the present invention for storing the alarm conditions in the form of alarm condition records. Each alarm condition record (corresponding to each row of the alarm table 150) may consist of one or more elements (corresponding to each column of the alarm table 150). The elements may include, but are not limited to, DATA_ITEM, ACTIVE, LOWER_ALARM_THRESHOLD, UPPER_ALARM_THRESHOLD, BASELINE, and CHANGE_ALARM_THRESHOLD.

A DATA_ITEM column 152 identifies the physiologic or parametric data items which have associated alarm conditions. For example, DATA_ITEM column 152 indicates that an alarm condition record 154 contains alarm conditions for the intrinsic atrial rate data item. An ACTIVE column 156 contains flags used by the programmer control unit 52 (FIG. 1) to determine whether a particular alarm condition record is active or suppressed. If the ACTIVE flag of a particular alarm condition record is set, the particular alarm condition record is considered to be a part of the alarm table 150. If the ACTIVE flag of a particular alarm condition record is not set, the particular alarm condition record is suppressed and is ignored by the programmer control unit 52 (FIG. 1) when the alarm table 150 is used to determine whether any alarm conditions are violated. For example, the alarm condition record 154 has its ACTIVE flag set, and thus it is used by the programmer control unit 52 (FIG. 1), while an alarm condition record 158 does not have its ACTIVE flag set, and thus it would be ignored by the programmer control unit 52 (FIG. 1).

The LOWER_ALARM_THRESHOLD column 160 represents the minimum values below which data item-values would be considered unusual, thus violating the alarm condition. For example, the LOWER_ALARM_THRESHOLD of the alarm condition record 154 is 40 bpm. Thus, if the intrinsic atrial rate fell below 40 bpm, the intrinsic atrial rate would be considered unusual and the LOWER_ALARM_THRESHOLD alarm condition would be violated. The UPPER_ALARM_THRESHOLD column 162 represents the maximum values above which data item values would be considered unusual, thus violating the alarm condition. For example, the UPPER_ALARM_THRESHOLD of the alarm condition record 154 is 180 bpm. Thus, if the intrinsic atrial rate rose above 180 bpm, the intrinsic atrial rate would be considered unusual and the UPPER_ALARM_THRESHOLD alarm condition would be violated.

The BASELINE column 164 is the value to which the values from one or more of a particular data item's data acquisition time columns 90-102 (described above in connection with FIG. 2) are compared. In this manner, changes in data items with associated BASELINEs may be identified. The BASELINE for the data item of a particular alarm condition record may be defined in accordance with one of several approaches depending on the nature of that data item.

In a first approach, the BASELINE may be a constant value pre-defined by the manufacturer of the implantable medical device 30 (FIG. 1). In a second approach, the BASELINE may be a value selected by the programmer control unit 52 (FIG. 1) from previously recorded values of that data item. The selection criteria for selecting a value from previously recorded values are preferably pre-defined by the manufacturer of the implantable medical device 30 (FIG. 1), and are preferably time-based. A typical selection criteria for a particular data item may be the value of that data item from 1 year ago. For example, the BASELINE for an alarm condition record 168, "battery impedance data item," is defined as the value of the battery impedance data item from one year ago. As a result, the recently acquired battery impedance data item would be compared to its value from one year ago. If the implantable medical device 30 (FIG. 1) has been implanted less than a year ago, the first recorded value of a data item may be used as a BASELINE. In a third approach, the BASELINE for a particular alarm condition record may be defined as a mathematical expression which operates on one or more previous values of that alarm condition record's data item. The mathematical expression BASELINE for a particular data item is preferably pre-determined by the manufacturer of the implantable medical device 30 (FIG. 1) in accordance with the nature of that data item. For example, the BASELINE for an alarm condition record 104 (atrial lead impedance data item) is defined as the linear regression of the previous atrial lead impedance values ending at measurement time minus 1 year or at 2 months after implantation, whichever is later.

The CHANGE_ALARM_THRESHOLD column 170 represents a maximum change in a particular data item's value with respect to that data item's BASELINE, above which the change would be considered unusual, thus violating the CHANGE_ALARM_THRESHOLD alarm condition. The CHANGE_ALARM_THRESHOLD may be a constant or a function defined by the manufacturer of the implantable medical device 30 (FIG. 1). An example of a CHANGE_ALARM_THRESHOLD which is a constant is the CHANGE_ALARM_THRESHOLD of the alarm condition record 168, which is 2 k$\Omega$. An example of a CHANGE_ALARM_THRESHOLD which is a function, is the CHANGE_ALARM_THRESHOLD of the alarm condition record 104, which is 250 $\Omega$ divided by the implant time in years.

A master alarm table (not shown, but identical to the alarm table 150 in format) is preferably pre-loaded by the manufacturer of the implantable medical device 30 (FIG. 1) with typical BASELINEs and alarm condition values and functions for various data items, including but not being limited to, LOWER_ALARM_THRESHOLDs, UPPER_ALARM_THRESHOLDs, and CHANGE_ALARM_THRESHOLDs.

When a new historical patient data file is created, a copy of the master alarm table (not shown) is made containing default values and is stored in the storage memory 56 (FIG. 1) as the alarm table 150. The medical practitioner may then customize the alarm table 150 (FIG. 3) for each patient by editing, disabling, or enabling the alarm conditions for all or some of the data items. The BASELINEs are typically defined by the commonly accepted medical community standards and thus should not be changed from pre-loaded values.

Referring now to FIGS. 4-7, a logic flow diagram representing a control program for the control unit 52 of FIG. 1 in accordance with a preferred embodiment of the present invention is described. After the medical practitioner begins the program at a step 200, the programmer control unit 52 (FIG. 1) acquires medical data from the implantable medical device 30 (FIG. 1) through telemetry at a step 202. The medical data may be acquired through telemetry locally by using the programmer telemetry head 60 (FIG. 1), or remotely through the data communication pathway 78 (FIG. 1) by using the modem 74 (FIG. 1) and the remote telemetry device 80 (FIG. 1).

Medical data may include, but are not limited to, inter-visit data (if any are present), identification data, and current physiologic and parametric data measured by the implantable medical device control unit 34 (FIG. 1) and stored in data item table 84 (FIG. 2). Inter-visit data for physiologic and parametric data items may be collected by the implantable medical device 30 (FIG. 1) between visits. An example of how data for certain parametric data items may be acquired between visits is disclosed in the above-incorporated U.S. Pat. No. 5,507,786. The recently acquired medical data are then temporarily stored in the programmer memory 54 (FIG. 1).

At a test 204, the programmer control unit 52 (FIG. 1) compares the acquired UIC against entries in a table of UICs stored in the storage memory 56 (FIG. 1). This step serves to ascertain whether the particular patient being examined has an existing historical patient data file in the programmer 32. If there is no match, the programmer control unit 52 (FIG. 1) adds the new UIC to the table of UICs at a step 206, and creates a new historical patient data file at a step 208. At the step 208, a new alarm table 150 (FIG. 3) for storing alarm condition records is created by duplicating the master alarm table (not shown). The alarm table 150 (FIG. 3) is then linked to the historical patient data file. Thus, each historical patient data file has an associated alarm table 150 (FIG. 3). The programmer control unit 52 (FIG. 1) then proceeds to a test 214.

However, if at the test 204, the UIC matches an entry in the table of existing UICs, the programmer control unit 52 (FIG. 1) locates the corresponding historical patient data file containing medical data from previous visits in the storage memory 56 (FIG. 1), and loads its contents and the linked alarm table 150 (FIG. 3) into the programmer memory 54 (FIG. 1) at a step 210. Of course, if the size of the historical patient data file exceeds memory capacity, the historical patient data file and the alarm table 150 (FIG. 3) may be loaded in portions or "swapped" from the larger capacity storage memory 56 (FIG. 1). The programmer control unit 52 (FIG. 1) then merges the medical data acquired from the implantable medical device 30 (FIG. 1) at the step 202 into the historical patient data file at a step 212 by placing inter-visit and current data for each data item into an appropriate data acquisition time column in the table 84 (FIG. 2). For example, if inter-visit values for an intrinsic atrial rate data item were 35, 38, and 189 bpm the programmer control unit 52 (FIG. 1) would place these values in the data acquisition time column 90 on the intrinsic atrial rate data item row 104 (FIG. 2), while the current measurement of the intrinsic atrial rate value of 89 bpm acquired during the step 202 would be placed into the data acquisition time column 92. The updated historical patient data file in the programmer memory 54 (FIG. 1) thus integrates medical data acquired during the present visit with medical data acquired during previous visits. Therefore, the medical practitioner has access to the patient's implantable medical device therapy history during the visit. The programmer control unit 52 (FIG. 1) then proceeds to the test 214.

At the test 214, the programmer control unit 52 (FIG. 1) prompts the medical practitioner to indicate whether further tests are to be performed. These tests may be typical physiologic data measurements made while the patient is stationary or may involve physiologic data measurements made while the patient is engaged in some calisthenic activity prescribed by the medical practitioner, such as running on a treadmill or breathing heavily.

The tests may also include diagnostic or calibration measurements of the implantable medical device 30 (FIG. 1) that were not performed automatically at the step 202. These tests may include verification of sensor parameter settings or capture threshold tests. The medical practitioner may also want the programmer 32 (FIG. 1) to repeat one or more previous physiologic measurements initially made by the implantable medical device 30 (FIG. 1) at the step 202, especially if a measurement appears unusual. If additional tests are to be performed, at a step 216, the programmer control unit 52 (FIG. 1) runs the requested tests and merges the results of the tests into the historical patient data file. The programmer control unit 52 (FIG. 1) may perform the tests by using the sensing circuit 44 (FIG. 1) through telemetry, by using the diagnostic circuit 70 (FIG. 1), or by using external diagnostic equipment (not shown). The programmer control unit 52 (FIG. 1) then proceeds to the step 212 in order to merge the data acquired during the tests into the historical patient data file. If no tests are to be performed, the programmer control unit 52 (FIG. 1) proceeds to a test 218 in FIG. 5.

At the test 218, the programmer control unit 52 (FIG. 1) queries the medical practitioner as to whether any alarm condition records in the alarm table 150 (FIG. 3) should be edited.

If any alarm conditions are to be edited, the programmer control unit 52 (FIG. 1) proceeds to a step 220. At the step 220, the medical practitioner is prompted to select an alarm condition record for editing. Once an alarm condition record is selected, the programmer control unit 52 (FIG. 1) proceeds to a step 222, where the medical practitioner may set or remove the ACTIVE flag for the alarm condition record being edited. As discussed above in connection with FIG. 3, removing the ACTIVE flag for a particular alarm condition record causes the programmer control unit 52 (FIG. 1) to ignore whether the alarm conditions defined in that alarm condition record are violated. The programmer control unit 52 (FIG. 1) then proceeds to a test 224.

Figure 8:
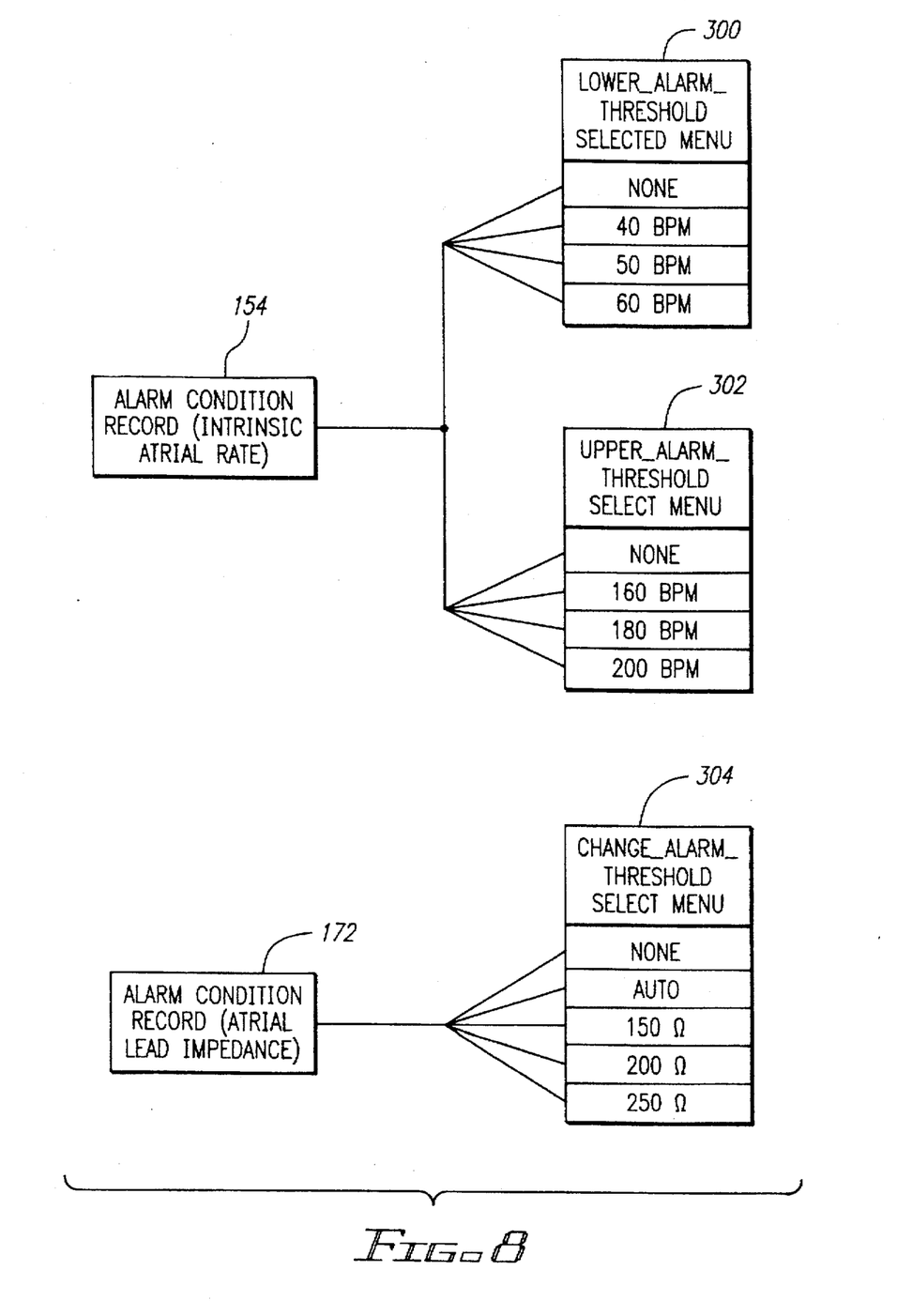
FIG. 8 depicts examples of menu structures for selecting alarm conditions from the alarm table which are applied to medical data in accordance with the principles of the present invention.

At the test 224, the programmer control unit 52 (FIG. 1) determines whether the alarm condition record being edited includes a LOWER_ALARM_THRESHOLD. If the alarm condition record does not include a LOWER_ALARM_THRESHOLD, the programmer control unit 52 (FIG. 1) proceeds to a test 230. If the alarm condition record includes a LOWER_ALARM_THRESHOLD, the programmer control unit 52 (FIG. 1) proceeds to a test 226, where the programmer control unit 52 (FIG. 1) queries the medical practitioner whether the LOWER_ALARM_THRESHOLD should be edited. If the LOWER_ALARM_THRESHOLD is to be edited, at a step 228 the medical practitioner is prompted by the programmer control unit 52 (FIG. 1) to select a new value for the LOWER_ALARM_THRESHOLD from a group of pre-defined values appropriate for the DATA_ITEM of the alarm condition record being edited, including a "null" value. If a "null" value is selected, the LOWER_ALARM_THRESHOLD will be disabled for that alarm condition record. Referring to FIG. 8, an example is shown of how the LOWER_ALARM_THRESHOLD value may be selected for the alarm condition record 154 (FIG. 3) for the intrinsic atrial rate DATA_ITEM. A LOWER_ALARM_THRESHOLD selection menu 300 provides four choices for the medical practitioner: "none," "40 bpm," "50 bpm," and "60 bpm." If the medical practitioner selects "none" as the LOWER_

ALARM_THRESHOLD value, the LOWER_ALARM_THRESHOLD for the alarm condition record being edited will be disabled, and the programmer control unit 52 (FIG. 1) will consider the alarm condition record as lacking a LOWER_ALARM_THRESHOLD element.

Returning now to FIG. 5, after completing the step 228, the programmer control unit 52 (FIG. 1) proceeds to the test 230. At the test 230 the programmer control unit 52 (FIG. 1) determines whether the alarm condition record being edited includes an UPPER_ALARM_THRESHOLD. If the alarm condition record does not include an UPPER_ALARM_THRESHOLD, the programmer control unit 52 (FIG. 1) proceeds to a test 236. If the alarm condition record includes an UPPER_ALARM_THRESHOLD, the programmer control unit 52 (FIG. 1) proceeds to a test 232, where the programmer control unit 52 (FIG. 1) queries the medical practitioner whether the UPPER_ALARM_THRESHOLD should be edited. If the UPPER_ALARM_THRESHOLD is to be edited, at a step 234 the medical practitioner is prompted by to the programmer control unit 52 (FIG. 1) to select a new value for the UPPER_ALARM_THRESHOLD from a group of values appropriate for the DATA_ITEM of the alarm condition record being edited, including a "null" value. If a "null" value is selected, the UPPER_ALARM_THRESHOLD will be disabled for that alarm condition record. Referring to FIG. 8, an example is shown of how the UPPER_ALARM_THRESHOLD value may be selected for the alarm condition record 154 (FIG. 3) for the intrinsic atrial rate DATA_ITEM. An UPPER_ALARM_THRESHOLD selection menu 302 provides four choices for the medical practitioner: "none," "160 bpm," "180 bpm," and "200 bpm." If the medical practitioner selects "none" as the UPPER_ALARM_THRESHOLD value, the UPPER_ALARM_THRESHOLD for the alarm condition record being edited will be disabled, and the programmer control unit 52 (FIG. 1) will consider the alarm condition record as lacking an UPPER_ALARM_THRESHOLD element.

Returning now to FIG. 5, after completing the step 234, the programmer control unit 52 (FIG. 1) proceeds to the test 236. At the test 236 the programmer control unit 52 (FIG. 1) determines whether the alarm condition record being edited includes a CHANGE_ALARM_THRESHOLD. If the alarm condition record does not include a CHANGE_ALARM_THRESHOLD, the programmer control unit 52 (FIG. 1) proceeds to a test 238 where the programmer control unit 52 (FIG. 1) queries the medical practitioner whether the alarm condition record editing process is complete. If the editing process is not complete, the programmer control unit 52 (FIG. 1) returns to the step 220 where the medical practitioner may select the next alarm condition record. If the alarm condition record includes a CHANGE_ALARM_THRESHOLD, the programmer control unit 52 (FIG. 1) proceeds to a test 240, where the programmer control unit 52 (FIG. 1) queries the medical practitioner whether the CHANGE_ALARM_THRESHOLD should be edited. If the CHANGE_ALARM_THRESHOLD is to be edited, at a step 242 the medical practitioner is prompted by the programmer control unit 52 (FIG. 1) to select a new value for the CHANGE_ALARM_THRESHOLD from a group of values appropriate for the DATA_ITEM of the alarm condition record being edited, including a "null" value. Since the CHANGE_ALARM_THRESHOLD may also be a function calculated by the programmer control unit 52 (FIG. 1), the medical practitioner may select the CHANGE_ALARM_THRESHOLD to be a predetermined function instead of a constant value. If a "null" value is selected, the CHANGE_ALARM_THRESHOLD will be disabled for that alarm condition record. Referring to FIG. 8, an example is shown of how the CHANGE_ALARM_THRESHOLD value may be selected for the alarm condition record 172 (FIG. 3) with the atrial lead impedance DATA_ITEM. A CHANGE_ALARM_THRESHOLD selection menu 304 provides five choices for the medical practitioner: "none," "AUTO," "150 Ω," "200 Ω," and "250 Ω." If the medical practitioner selects "none" as the CHANGE_ALARM_THRESHOLD value, the CHANGE_ALARM_THRESHOLD for the alarm condition record being edited will be disabled, and the programmer control unit 52 (FIG. 1) will consider the alarm condition record as lacking a CHANGE_ALARM_THRESHOLD element. Selecting "AUTO" will set the CHANGE_ALARM_THRESHOLD to a predetermined function. For example, alarm condition record 172 (FIG. 3) has a CHANGE_ALARM_THRESHOLD which is a function—250 Ω divided by the implant time in years. Selecting any of the other values will set the CHANGE_ALARM_THRESHOLD to that value. Returning now to FIG. 5, after completing the step 242, the programmer control unit 52 (FIG. 1) returns to the test 238 where the medical practitioner is queried whether the editing process is complete.

Figure 6:
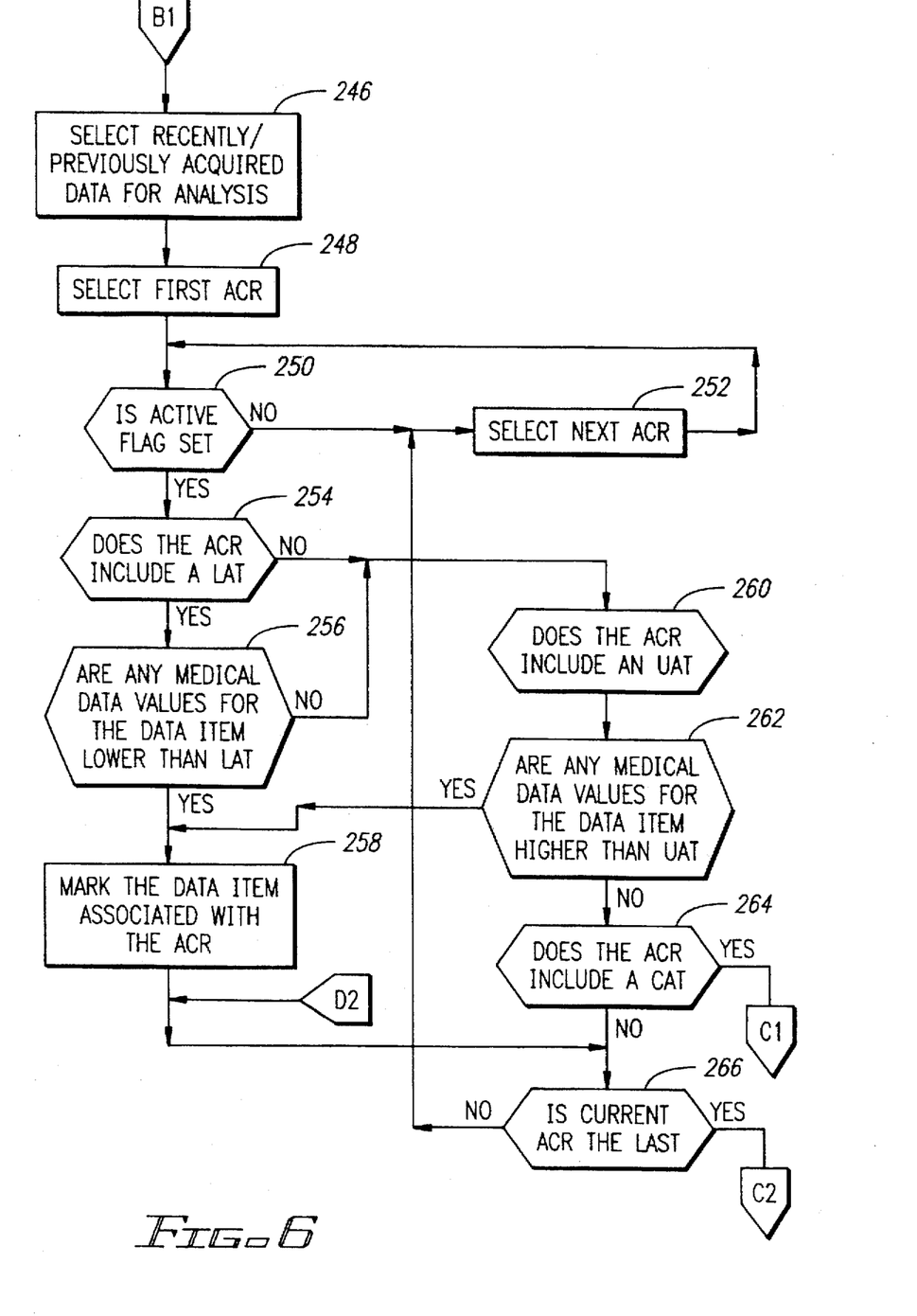

If, at the test 238, the medical practitioner decides that the editing process is complete, the programmer control unit 52 (FIG. 1) proceeds to a step 246 in FIG. 6.

Referring now to FIG. 6, at the step 246 the programmer control unit 52 (FIG. 1) prompts the medical practitioner to select medical data to be used in determining whether the alarm conditions in any of the alarm condition records are violated, by selecting one or more data acquisition time columns from the table 84 (FIG. 2). For example, if the medical practitioner wants to analyze only recently acquired medical data, only data acquisition time columns 90 and 92 (FIG. 2) would be selected at the step 246.

The programmer control unit 52 (FIG. 1) then proceeds to a step 248, where the programmer control unit 52 (FIG. 1) selects the first alarm condition record in the alarm table 150 (FIG. 3). At a test 250, the programmer control unit 52 (FIG. 1) determines whether the ACTIVE flag of the currently selected alarm condition record is set. If the ACTIVE flag is not set, the programmer control unit 52 (FIG. 1) proceeds to a step 252 where the programmer control unit 52 (FIG. 1) selects the next alarm condition record. If the ACTIVE flag is set, the programmer control unit 52 (FIG. 1) proceeds to a test 254.

At the test 254, the programmer control unit 52 (FIG. 1) determines whether the current alarm condition record includes a LOWER_ALARM_THRESHOLD. An alarm condition record may lack a LOWER_ALARM_THRESHOLD because some data items may not have an associated LOWER_ALARM_THRESHOLD, or because the LOWER_ALARM_THRESHOLD may be disabled (i.e., the LOWER_ALARM_THRESHOLD was set to "none" at the step 228 (FIG. 5)). If the current alarm condition record does not include a LOWER_ALARM_THRESHOLD, the programmer control unit 52 (FIG. 1) proceeds to a test 260. If the current alarm condition record includes a LOWER_ALARM_THRESHOLD, the programmer control unit 52 (FIG. 1) proceeds to a test 256. At the test 256, the programmer control unit 52 (FIG. 1) compares all values from the data selected at the step 246 for the data item under test with that data item's LOWER_ALARM_THRESHOLD from the alarm table 150 (FIG. 3). For example, if the current alarm condition record is the alarm condition record 154 (FIG. 3), and only recently acquired data was selected at the step 246, the following intrinsic atrial rate values would be compared to the alarm condition record 154 LOWER_ALARM_THRESHOLD (40 bpm): 35, 38, 180, and 89 bpm. If any of the values of the data selected at the step 246 are less than the LOWER_ALARM_THRESHOLD, the programmer control unit 52 (FIG. 1) proceeds to a step 258. This indicates that the LOWER_ALARM_THRESHOLD has been violated. In the above example, two data item values violate the LOWER_ALARM_THRESHOLD—35 and 38 bpm.

At the step 258, the programmer control unit 52 (FIG. 1) marks the data item violating any of the alarm conditions of the selected alarm condition record. The marking function may be performed in a number of well-known ways, such as using a programmer control unit 52 (FIG. 1) flag, or by setting a "marked" variable for a data item to a value of "1" if the data item is to be marked, where a marked variable with a value of "0" indicates that a data item is unmarked.

If none of the values of the data selected at the step 246 are less than the LOWER_ALARM_THRESHOLD, the programmer control unit 52 (FIG. 1) proceeds to the test 260.

At the test 260, the programmer control unit 52 (FIG. 1) determines whether the current alarm condition record includes an UPPER_ALARM_THRESHOLD. An alarm condition record may lack the UPPER_ALARM_THRESHOLD because some data items may not have an associated UPPER_ALARM_THRESHOLD, or because the UPPER_ALARM_THRESHOLD may be disabled (i.e., the UPPER_ALARM_THRESHOLD was set to "none" at the step 232 (FIG. 5)). If the current alarm condition record does not include an UPPER_ALARM_THRESHOLD, the programmer control unit 52 (FIG. 1) proceeds to a test 264. If the current alarm condition record includes an UPPER_ALARM_THRESHOLD, the programmer control unit 52 (FIG. 1) proceeds to a test 262. At the test 262, the programmer control unit 52 (FIG. 1) compares all values from the data selected at the step 246 for the data item under test with that data item's UPPER_ALARM_THRESHOLD from the alarm table 150 (FIG. 3). For example, if the current alarm condition record is the alarm condition record 154 (FIG. 3), and only recently acquired data was selected at the step 246, the following intrinsic atrial rate values would be compared to the alarm condition record 154 UPPER_ALARM_THRESHOLD (180 bpm): 35, 38, 180, and 89 bpm. If any of the values of the data selected at the step 246 exceed the UPPER_ALARM_THRESHOLD, the programmer control unit 52 (FIG. 1) proceeds to a step 258. This indicates that the UPPER_ALARM_THRESHOLD has been violated. In the above example, none of the data item values violate the UPPER_ALARM_THRESHOLD. If none of the values of the data selected at the step 246 exceed the UPPER_ALARM_THRESHOLD, the programmer control unit 52 (FIG. 1) proceeds to the test 264.

At the test 264, the programmer control unit 52 (FIG. 1) determines whether the current alarm condition record includes a CHANGE_ALARM_THRESHOLD. An alarm condition record may lack a CHANGE_ALARM_THRESHOLD because some data items may not have an associated CHANGE_ALARM_THRESHOLD, or because the CHANGE_ALARM_THRESHOLD may be disabled (i.e., the CHANGE_ALARM_THRESHOLD was set to "none" at the step 242). If the current alarm condition record does not include a CHANGE_ALARM_THRESHOLD, the programmer control unit 52 (FIG. 1) proceeds to a test 266.

At the test 266, the programmer control unit 52 (FIG. 1) determines if the current alarm condition record is the last one in the alarm table 150 (FIG. 3). If the current alarm condition record is not the last one, the programmer control unit 52 (FIG. 1) returns to the step 252, where the next alarm condition record will be selected. If the current alarm condition record is the last one, the programmer control unit 52 (FIG. 1) proceeds to a step 278 in FIG. 7.

Figure 7:
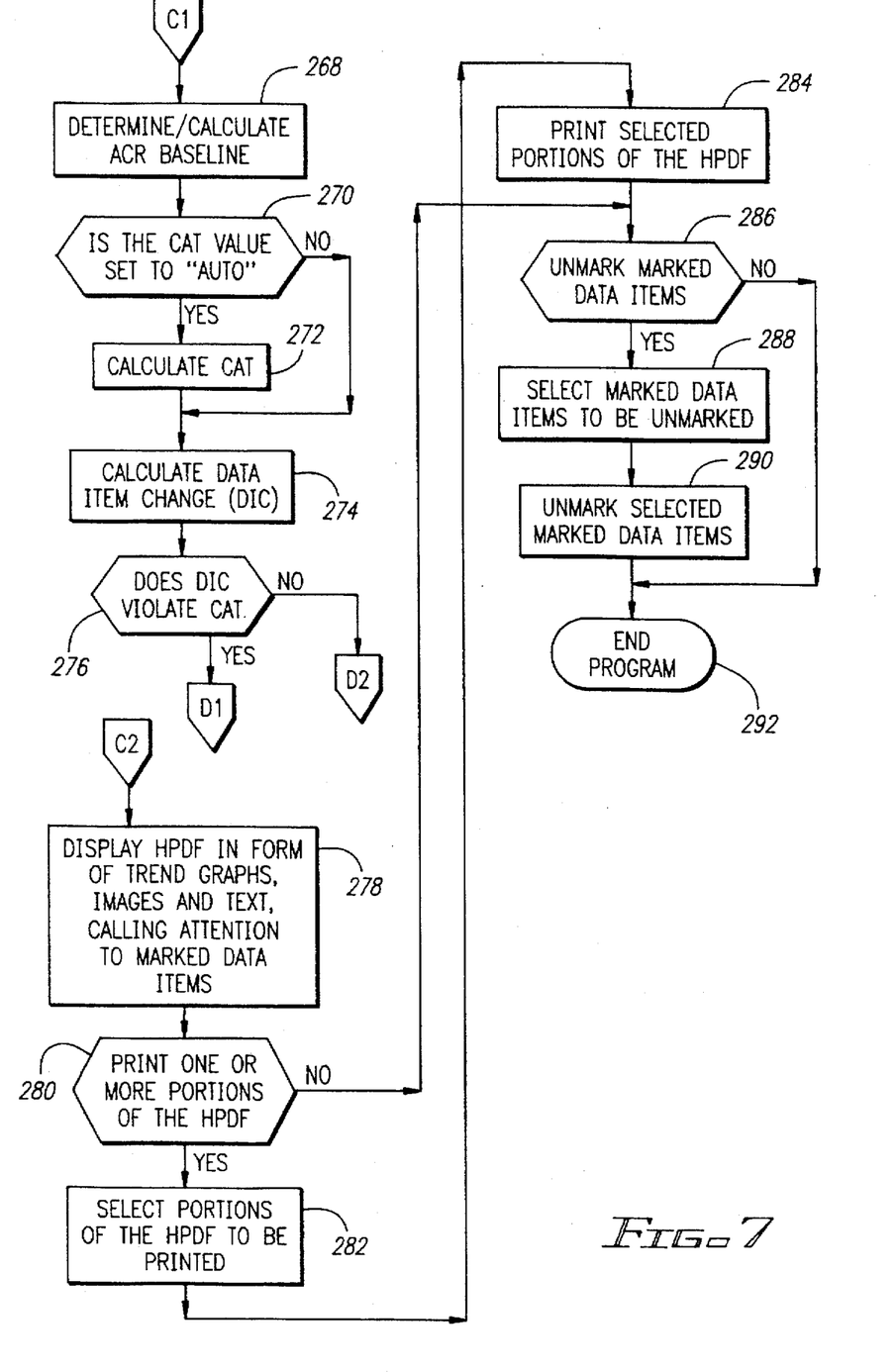

If the alarm condition record includes a CHANGE_ALARM_THRESHOLD, the programmer control unit 52 (FIG. 1) proceeds to a step 268 in FIG. 7.

Referring now to FIG. 7, at the step 268, the programmer control unit 52 (FIG. 1) determines the BASELINE of the current alarm condition by retrieving an appropriate BASELINE value from past values of the current alarm condition's data item, or calculates the BASELINE if it is a function. For example, if the current alarm condition record is the alarm condition record 154 (FIG. 3), the BASELINE is a linear regression function which must be calculated. However, if the current alarm condition record is the alarm condition record 168 (FIG. 3), the BASELINE is simply the battery impedance value from 1 year ago, which according to table 84 (FIG. 2), is 28 kΩ, assuming visits occur every three months. If the BASELINE is a constant, the programmer control unit 52 (FIG. 1) retrieves the value of the BASELINE.

At a test 272, the programmer control unit 52 (FIG. 1) determines whether the CHANGE_ALARM_THRESHOLD of the current alarm condition record was set to "AUTO" in the step 242 (FIG. 5) thus requiring calculation. If the CHANGE_ALARM_THRESHOLD was set to "AUTO," the programmer control unit 52 (FIG. 1) proceeds to a step 272, where the CHANGE_ALARM_THRESHOLD is calculated. Otherwise the programmer control unit 52 (FIG. 1) proceeds to a step 274. At the step 274, the change in the current alarm condition record's data item is calculated by taking an absolute value of the difference between one or more values from the data selected at the step 246 and the current data item's BASELINE. If the data selected at the step 246 contains multiple values for the data item being tested several data item changes may be obtained. At a test 276, the programmer control unit 52 (FIG. 1) compares all data item changes determined in the step 274 with that data item's CHANGE_ALARM_THRESHOLD. If any of the data item changes exceed the CHANGE_ALARM_THRESHOLD, the programmer control unit 52 (FIG. 1) proceeds to the step 258 (FIG. 6). This indicates that the CHANGE_ALARM_THRESHOLD has been violated. If none of the data item changes exceed the CHANGE_ALARM_THRESHOLD, the programmer control unit 52 (FIG. 1) proceeds to a test 266 (FIG. 6).

Figure 9:
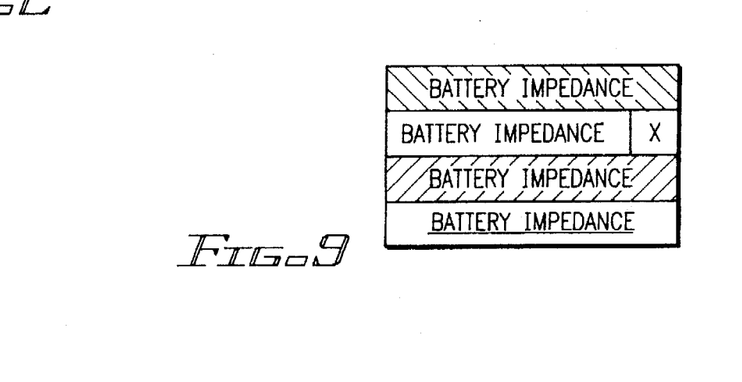
FIG. 9 depicts examples of attention-attracting displays for medical data items identified as being in violation of programmable alarm conditions in accordance with the principles of the present invention.

At the step 278 the historical patient data file stored in the programmer memory 54 (FIG. 1) is displayed to the medical practitioner. In addition, if any physiologic and parametric data items were marked at the step 258 (FIG. 6), the marked data items are brought to the medical practitioner's attention by displaying them in an attention-attracting format. Attention-attracting formats may include, but are not limited to, bold text, reverse video display, flashing, and special graphics characters appearing next to the marked data items. Examples of several attention-attracting display formats are shown in FIG. 9 for the battery impedance data item row 110 (FIG. 2).

Since the viewing area of the graphical display unit 58 (FIG. 1) may be limited, the medical practitioner may need to move through several screens to view all the information.

For example, the first screen may contain all the identification information, such as the patient's background information. The second screen may display physiologic data items, while the third screen may display parametric data items. The user input device 62 (FIG. 1) allows the medical practitioner to navigate through the various screens.

At a test 280, the programmer control unit 52 (FIG. 1) prompts the medical practitioner to indicate whether portions of the historical patient data file are to be printed. If printing is requested, at a step 282 the medical practitioner selects either the entire historical patient data file or certain portions of the file, such as physiologic data items, parametric data items, and identification data in any combination. For example, if the medical practitioner wishes to examine only parametric data items, the practitioner may choose to print only those data items. Or, optionally, specific graphs, images or text fields may be selected from various portions of the historical patient data file. In addition, the medical practitioner may choose to print only the marked physiologic and parametric data items. This approach gives the medical practitioner the flexibility of printing only the information that is of interest without having to print the entire historical patient data file, which can be quite time consuming. At a step 284, the selected portions of the historical patient data file are printed on the printer 66 (FIG. 1). If no printing is requested at the test 280, the programmer control unit 52 (FIG. 1) proceeds to a test 286.

At the test 286, the programmer control unit 52 (FIG. 1) prompts the medical practitioner to indicate whether any of the marked data items should be unmarked. If any of the marked data items are to be unmarked, the programmer control unit 52 (FIG. 1) proceeds to a step 288 where the medical practitioner selects the marked data items to be unmarked. The medical practitioner also may have an option to "unmark all" which would select all marked data items to be unmarked. At a step 290, the programmer control unit 52 (FIG. 1) unmarks marked data items selected by the medical practitioner in the step 288. If none of the marked data items are to be unmarked, the programmer control unit 52 (FIG. 1) proceeds to a step 292. At the step 292 the programmer control unit 52 (FIG. 1) ends the program and returns to the initial display screen (not shown) on the display unit 58 (FIG. 1) where the medical practitioner may begin another program.

Thus a system and method for identifying and displaying medical data which violates at least one programmable threshold are provided. One skilled in the art will appreciate that the present invention can be practiced by other than the described embodiments, which are presented for purposes of illustration and not of limitation, and the present invention is limited only by the claims that follow.

What is claimed is:

1. A diagnostic system for use with an implantable medical device, the system comprising:

telemetry means for receiving medical data transmitted by the medical device;

means for defining at least one alarm condition;

long-term storage means for storing the at least one alarm condition;

first control means for applying the at least one alarm condition to the medical data to determine if any medical data values violate at least one alarm condition; and second control means for marking portions of the medical data which violate at least one alarm condition.

2. The system of claim 1, wherein the medical data comprise at least one data item, each of the at least one data items comprising at least one medical data value.

3. The system of claim 2, wherein the portions of the medical data marked by the second control means comprise at least one data item having one or more of the at least one medical data values which violate the at least one alarm condition.

4. The system of claim 3, further comprising first selection means for selecting the at least one medical data value from each of the at least one data items, wherein each of the at least one medical data values is at least one of:

(a) recently acquired medical data values received during a current transmission of medical data from the implantable medical device, and (b) previously acquired medical data values received during a previous transmission of medical data from the implantable medical device.

5. The system of claim 4, further comprising:

means for defining at least one alarm condition record;

second selection means for selecting a data item from the at least one data items;

third selection means for selecting an alarm condition record from at the least one alarm condition records;

means for associating the selected alarm condition record with the selected data item; and means for associating one or more of the at least one alarm condition with the selected at least one alarm condition record, wherein the first control means applies one or more of the selected alarm condition record's at least one alarm condition to the at least one medical data value selected by the first selection means to determine if the selected at least one medical data value violates one or more of the at least one alarm condition.

6. The system of claim 5, wherein each of the at least one alarm condition associated with the at least one alarm condition record is at least one of: (a) a lower alarm threshold, (b) an upper alarm threshold, and (c) a change alarm threshold.

7. The system of claim 6, wherein if the at least one alarm condition comprises the lower alarm threshold, the system further comprises fifth selection means for selecting the lower alarm threshold from a lower alarm threshold set comprising at least one lower alarm threshold, such that when the first control means applies the selected lower alarm threshold to the at least one medical data value selected by the first selection means, and the at least one selected medical data value comprises at least one medical data value which is lower than the selected lower alarm threshold, the first control means determines that the associated data item has at least one medical data value which violates the at least one alarm condition.

8. The system of claim 7, wherein the lower alarm threshold set further comprises a null value, such that if the null value is selected by the fifth selection means for the lower alarm threshold, the first control means does not apply the lower alarm threshold to the at least one medical data value selected by the first selection means.

9. The system of claim 6, wherein if the at least one alarm condition comprises the upper alarm threshold, the system further comprises sixth selection means for selecting the upper alarm threshold from an upper alarm threshold set comprising at least one upper alarm threshold, such that when the first control means applies the selected upper alarm threshold to the at least one medical data value selected by the first selection means, and the selected at least one medical data value comprises at least one medical data value which is higher than the selected upper alarm threshold, the first control means determines that the associated data item has at least one medical data value which violates the at least one alarm condition.

10. The system of claim 9, wherein the upper alarm threshold set further comprises a null value, such that if the null value is selected by the sixth selection means for the upper alarm threshold, the first control means does not apply the upper alarm threshold to the at least one medical data value selected by the first selection means.

11. The system of claim 6, further comprising means for determining a baseline, and means for associating the baseline with the selected alarm condition record if the selected alarm condition record comprises the change alarm threshold.

12. The system of claim 11, wherein the means for determining a baseline sets the baseline to a constant value.

13. The system of claim 12, wherein the means for determining a baseline derives the baseline for the selected alarm condition record from at least one previously acquired medical value.

14. The system of claim 13, further comprising third control means for determining at least one data item change value, wherein the at least one data item change value is representative of the difference between each of the at least one medical data values selected by the first selection means, and the selected data item alarm condition record's associated baseline.

15. The system of claim 14, wherein the system further comprises seventh selection means for selecting the change alarm threshold from a change alarm threshold set comprising at least one change alarm threshold, such that when the first control means applies the selected change alarm threshold to the associated data item's at least one data item change value, and the at least one data item change value is higher than the selected change alarm threshold, the first control means determines that the associated data item has at least one data item change value which violates the at least one alarm condition.

16. The system of claim 15, wherein the change alarm threshold set further comprises a null value, such that if the null value is selected by the seventh selection means for the change alarm threshold, the first control means does not apply the change alarm threshold to the at least one medical data value selected by the first selection means.

17. The system of claim 16, wherein the change alarm threshold set further comprises means for deriving the change alarm threshold.

18. The system of claim 4, wherein each of the at least one alarm condition records further comprises an activity flag, wherein the system further comprises fourth selection means for setting and removing and removing the activity flag, and wherein:
when the activity flag is set for the selected alarm condition record, the first control means applies one or more of the selected alarm condition record's at least one alarm condition to that alarm condition record's associated data item to determine if the at least one medical data value selected by the first selection means violates one or more of the ay least one alarm condition, and
when the activity flag is not set for the selected alarm condition record, the first control means does not apply the selected alarm condition record's at least one alarm condition to that alarm condition record's associated data item.

19. The system of claim 3, further comprising display means which, under control of the second control means, displays each of the at least one marked data items in an attention-attracting format.

20. The system of claim 19, wherein the attention-attracting format is one of: (a) bold display, (b) a reverse video display, (c) a flashing display, (d) a display of a particular color, and (e) a display marked with at least one graphical character.

21. The system of claim 3, further comprising:
eighth selection means for selecting at least one marked data item; and
fifth control means for unmarking each of the selected at least one marked data items.

22. A diagnostic method for use with a medical device implanted in a patient, the method comprising the steps of:
telemetrically receiving medical data transmitted by the medical device;
defining at least one alarm condition;
storing the at least one alarm condition;
applying the at least one alarm condition to the medical data to determine if any medical data values violate one of more of the at least one alarm condition; and
marking portions of the medical data having values which violate one or more of the at least one alarm condition.

23. The method of claim 22, wherein the medical data comprise at least one data item, each of the at least one data items comprising at least one medical data value.

24. The method of claim 23, wherein the portions of the marked medical data comprise at least one data item having one or more of the at least one medical data values which violate the at least one alarm condition.

25. The method of claim 24, further comprising the step of selecting the at least one medical data value from each of the at least one data items, wherein each of the at least one medical data values is at least one of:
(a) recently acquired medical data values received during a current transmission of medical data from the implantable medical device, and
(b) previously acquired medical data values received during a previous transmission of medical data from the implantable medical device.

26. The method of claim 25, further comprising the steps of:
defining at least one alarm condition record;
selecting a data item from the at least one data items;
selecting an alarm condition record from at the least one alarm condition records;
associating the selected alarm condition record with the selected data item; and
associating one or more of the at least one alarm condition with the selected at least one alarm condition record;
applying one or more of the selected alarm condition record's at least one alarm condition to the selected at least one medical data value to determine if the selected at least one medical data value violates one or more of the at least one alarm condition.

27. The method of claim 26, wherein each of the at least one alarm condition associated with the at least one alarm condition record is at least one of: (a) a lower alarm threshold, (b) an upper alarm threshold, and a (c) change alarm threshold.

28. The method of claim 27, wherein if the at least one alarm condition comprises the lower alarm threshold, the method further comprises the steps of:
selecting the lower alarm threshold from a lower alarm threshold set comprising at least one lower alarm threshold;

applying the selected lower alarm threshold to the selected at least one medical data value; and determining if the selected at least one medical data value violates the at least one alarm condition by determining if the selected at least one medical data value comprises at least one medical data value which is lower than the selected lower alarm threshold.

29. The method of claim 28, wherein the lower alarm threshold set further comprises a null value, such that if the null value is selected for the lower alarm threshold, the lower alarm threshold is not applied to the selected at least one medical data value.

30. The method of claim 27, wherein if the at least one alarm condition comprises the upper alarm threshold, the method further comprises the steps of:

selecting the upper alarm threshold from an upper alarm threshold set comprising at least one upper alarm threshold;

applying the selected upper alarm threshold to the selected at least one medical data value; and determining if the selected at least one medical data value violates the at least one alarm condition by determining if the selected at least one medical data value comprises at least one medical data value which is higher than the selected upper alarm threshold.

31. The method of claim 30, wherein the upper alarm threshold set further comprises a null value, such that if the null value is selected for the upper alarm threshold, the upper alarm threshold is not applied to the selected at least one medical data value.

32. The method of claim 27, further the steps of:

determining a baseline; and associating the baseline with the selected alarm condition record if the selected alarm condition record comprises the change alarm threshold.

33. The method of claim 32, wherein the step of determining a baseline comprises setting the baseline to a constant value.

34. The method of claim 33, further comprising the step of determining at least one data item change value, wherein the at least one data item change value is representative of the difference between each of the selected at least one medical data values, and the selected data item alarm condition record's associated baseline.

35. The method of claim 34, further comprising the steps of:

selecting the change alarm threshold from a change alarm threshold set comprising at least one change alarm threshold;

applying the selected change alarm threshold to the associated data item's at least one data item change value; and determining if the at least one data item change value violates the at least one alarm condition by determining if the at least one data item change value is higher than the selected change alarm threshold.

36. The method of claim 35, wherein the change alarm threshold set further comprises a null value, such that if the null value is selected for the change alarm threshold, the change alarm threshold is not applied to the selected at least one medical data value.

37. The method of claim 36, wherein the change alarm threshold set further comprises the step of deriving the change alarm threshold.

38. The method of claim 32, wherein the step of determining a baseline comprises the step of deriving the baseline for the selected alarm condition record from an at least one previously acquired medical value.

39. The method of claim 25, wherein each of the at least one alarm condition records further comprises an activity flag, wherein the method further comprises the step of controlling the activity flag, and wherein:

when the activity flag is set for the selected alarm condition record, one or more of the selected alarm condition record's at least one alarm condition are applied to that alarm condition record's associated data item to determine if the selected at least one medical data value violates one or more of the at least one alarm condition, when the activity flag is not set for the selected alarm condition record, the selected alarm condition record's at least one alarm condition is not applied to that alarm condition record's associated data item.

40. The method of claim 22, further comprising the step of displaying each of the at least one marked data items in an attention-attracting format.

41. The method of claim 40, wherein the attention-attracting format is one of: (a) bold display, (b) a reverse video display, (c) a flashing display, (d) a display of a particular color, and (e) a display marked with at least one graphical character.

42. The method of claim 22, further comprising the steps of:

selecting at least one marked data item; and unmarking each of the selected at least one marked data items.

* * * * *